United States Patent
Archibald et al.

[11] Patent Number: 6,132,382
[45] Date of Patent: Oct. 17, 2000

[54] NON-INVASIVE BLOOD PRESSURE SENSOR WITH MOTION ARTIFACT REDUCTION

[75] Inventors: G. Kent Archibald, Vadnais Heights; Timothy G. Curran, Ramsey; Orland H. Danielson, Roseville; Marius O. Poliac, St. Paul; Roger C. Thede, Afton, all of Minn.

[73] Assignee: Medwave, Inc., Arden Hills, Minn.

[21] Appl. No.: 09/174,164

[22] Filed: Oct. 16, 1998

[51] Int. Cl.[7] ........................................... A61B 5/00
[52] U.S. Cl. ........................... 600/485; 600/500; 600/503
[58] Field of Search ........................... 600/485, 493–496, 600/500, 503, 561

[56] References Cited

U.S. PATENT DOCUMENTS

| | | | |
|---|---|---|---|
| 4,295,471 | 10/1981 | Kaspari | 600/500 |
| 4,409,983 | 10/1983 | Albert | 600/503 |
| 5,181,517 | 1/1993 | Hickey | 600/500 |
| 5,406,952 | 4/1995 | Barnes et al. | 600/503 |
| 5,427,109 | 6/1995 | Frankenreiter | 600/494 |
| 5,431,170 | 7/1995 | Mathews | 600/500 |
| 5,494,043 | 2/1996 | O'Sullivan et al. | 600/500 |
| 5,807,267 | 9/1998 | Bryars et al. | 600/503 |

*Primary Examiner*—Robert L. Nasser
*Attorney, Agent, or Firm*—Kinney & Lange

[57] ABSTRACT

A non-invasive blood pressure sensor includes a first fluid filled sensing chamber having a diaphragm. A first transducer is fluidly coupled to the first sensing chamber to sense fluid pressure within the first chamber. A flexible body conformable wall surrounds the sensing chamber. The wall applies force to the artery while preventing pressure in a direction generally parallel to the artery from being applied to the sensing chamber. The flexible body conformable wall includes a second fluid filled chamber. A second transducer fluidly coupled to the second chamber sensing fluid pressure within the second chamber. As varying pressure is applied to the artery pressure waveforms are sensed by the first transducer. Using output signals of the first and second transducers, the sensed pressure waveform data is analyzed to derive waveform parameters from which blood pressure values are derived. The effects of motion artifacts are reduced by the use of signals from both the first and second transducers.

26 Claims, 10 Drawing Sheets

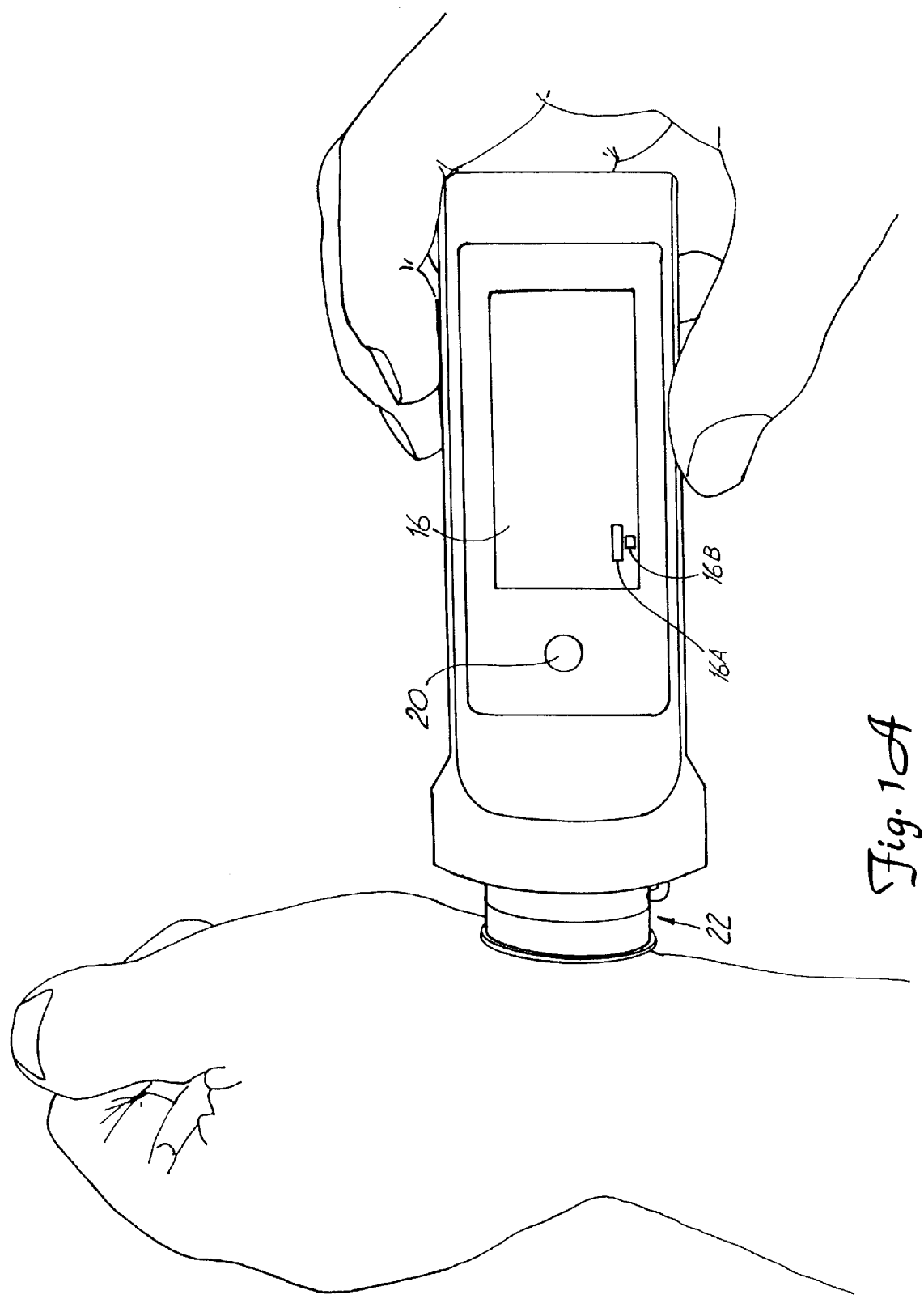

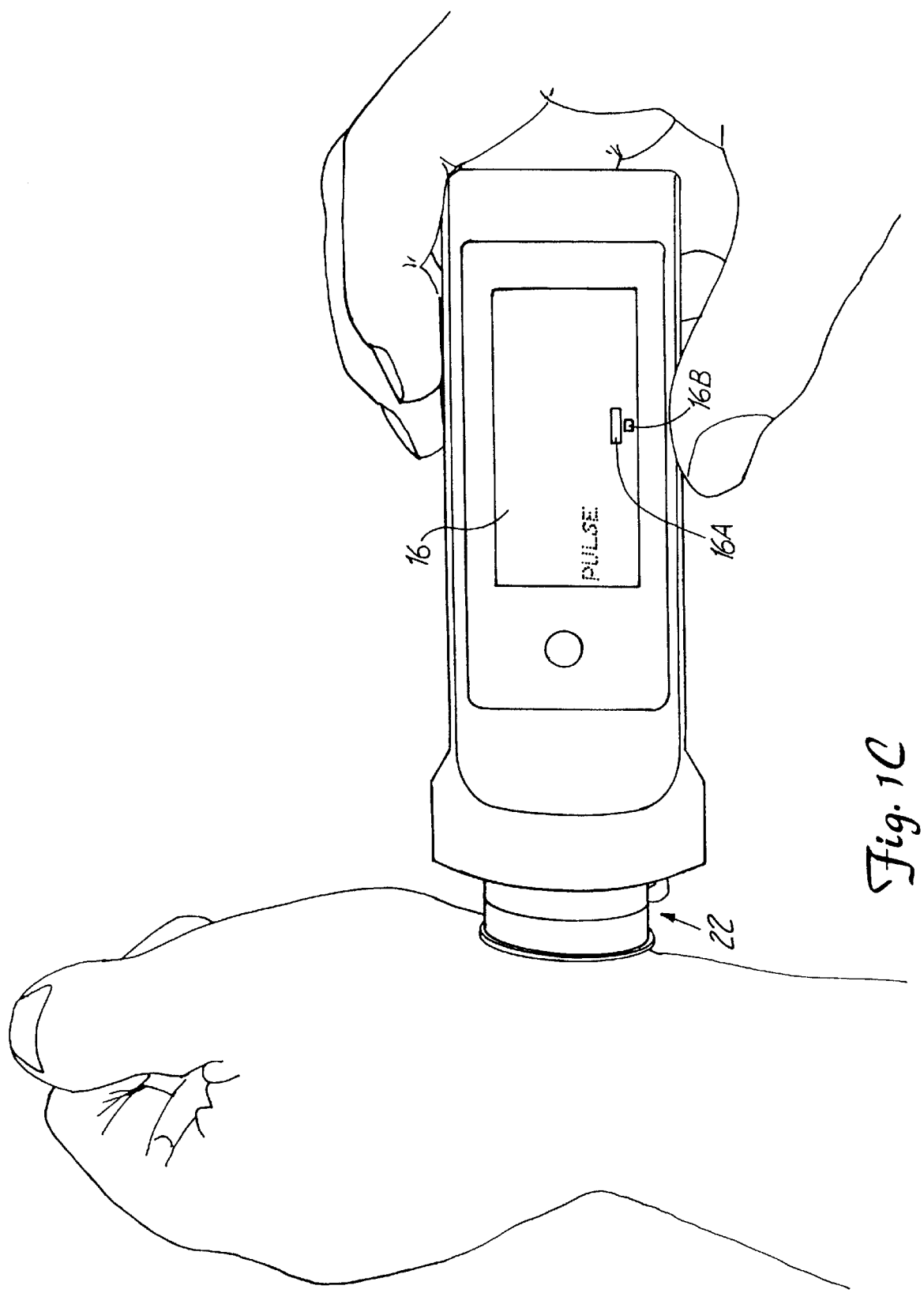

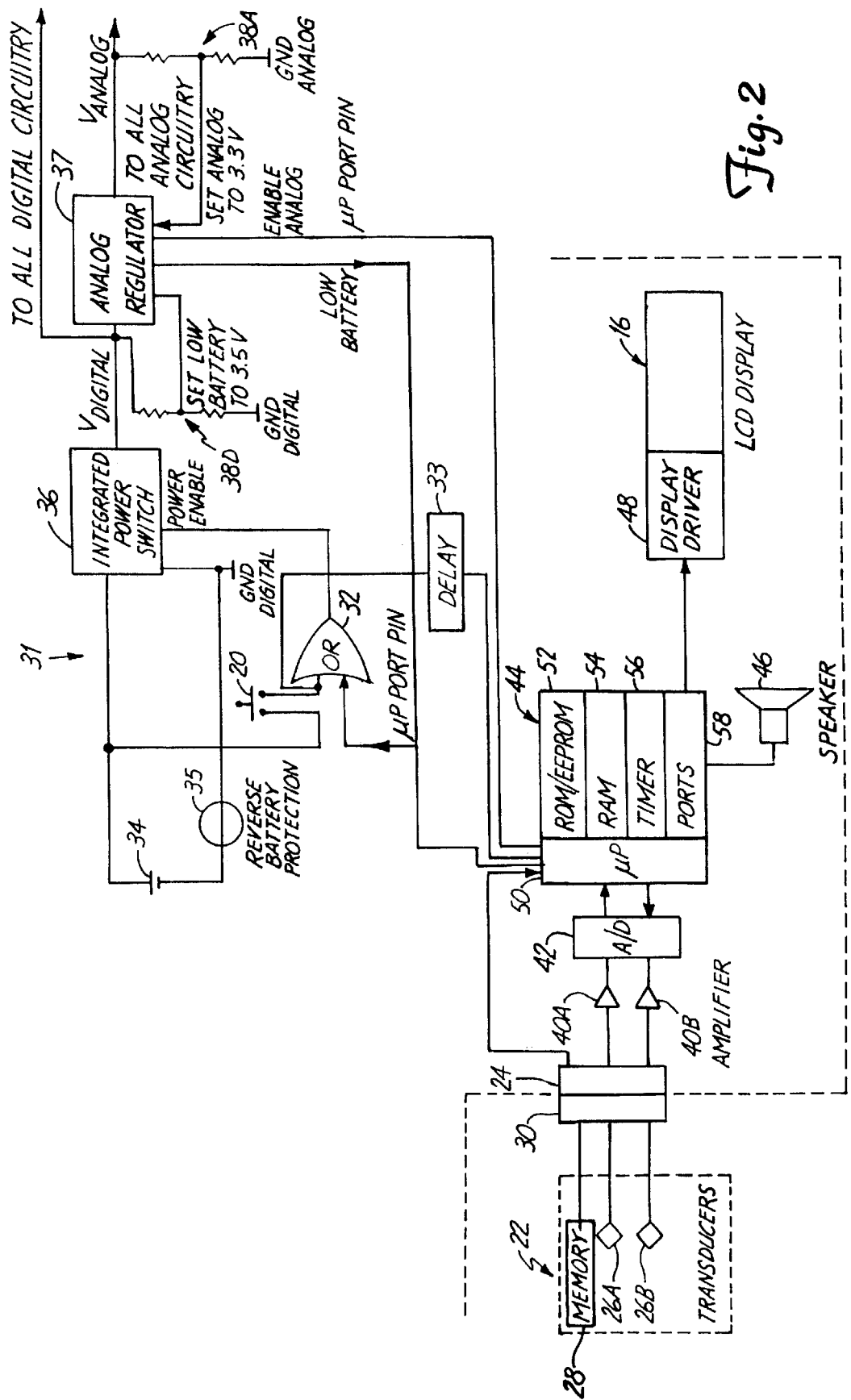

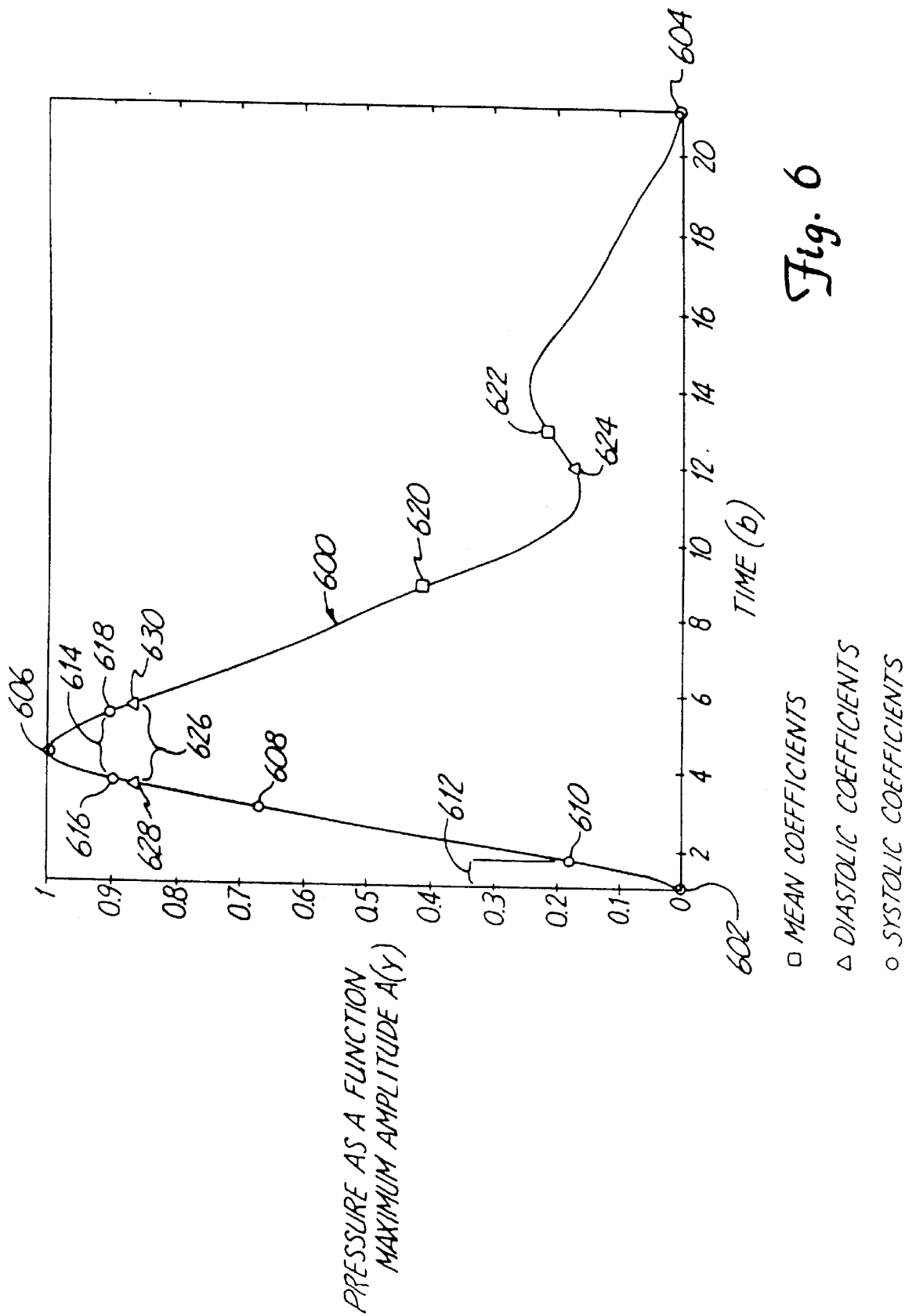

NON-INVASIVE BLOOD PRESSURE SENSOR WITH MOTION ARTIFACT REDUCTION

CROSS-REFERENCE TO RELATED APPLICATION(S)

None.

BACKGROUND OF THE INVENTION

The present invention relates to systems and devices for measuring arterial blood pressure. In particular, the invention relates to an improved method and device for measuring arterial blood pressure in a non-invasive manner while reducing the effects of motion artifacts.

There has been a continuing need for devices which will measure blood pressure non-invasively, with accuracy comparable to invasive methods. Medwave, Inc. the assignee of the present invention, has developed non-invasive blood pressure measurement devices which are described in the following United States patents: U.S. Pat. No. 5,649,542 entitled CONTINUOUS NON-INVASIVE BLOOD PRESSURE MONITORING SYSTEM; U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,720,292 entitled BEAT ONSET DETECTOR; U.S. Pat. No. 5,738,103 entitled SEGMENTED ESTIMATION METHOD; U.S. Pat. No. 5,722,414 entitled CONTINUOUS NON-INVASIVE BLOOD PRESSURE MONITORING SYSTEM; U.S. Pat. No. 5,642,733 entitled BLOOD PRESSURE SENSOR LOCATOR; and U.S. Pat. No. 5,797,850 entitled METHOD AND APPARATUS FOR CALCULATING BLOOD PRESSURE OF AN ARTERY. Further description of these devices is found in U.S. patent application Ser. No. 08/912,139 filed Aug. 15, 1997, entitled HAND-HELD NON-INVASIVE BLOOD PRESSURE MEASUREMENT DEVICE.

As described in these patents and the pending patent application, the Medwave non-invasive blood pressure measurement device and method determines blood pressure by sensing pressure waveform data derived from an artery. A pressure sensing device includes a sensing chamber with a diaphragm which is positioned over the artery. A transducer coupled to the sensing chamber senses pressure within the chamber. A flexible body conformable wall is located adjacent to (and preferably surrounding) the sensing chamber. The wall is isolated from the sensing chamber and applies force to the artery while preventing pressure in a direction generally parallel to the artery from being applied to the sensing chamber.

As varying pressure is applied to the artery by the sensing chamber, pressure waveforms are sensed by the transducer to produce sensed pressure waveform data. The varying pressure may be applied automatically in a predetermined pattern, or may be applied manually in a somewhat random fashion.

The sensed pressure waveform data is analyzed to determine waveform parameters which relate to the shape of the sensed pressure waveforms. One or more blood pressure values are derived based upon the waveform parameters. The Medwave blood pressure measurement devices include both automated devices for continuously monitoring blood pressure (such as in a hospital setting) and hand-held devices which can be used by a physician, or by a patient when desired. These devices represent an important improvement in the field of non-invasive blood pressure measurement. Still further improvements, of course, are highly desirable.

BRIEF SUMMARY OF THE INVENTION

The present invention is an improvement to a non-invasive blood pressure sensing device and method of the type having a fluid filled sensing chamber and a flexible body conformable wall proximate to and isolated from the sensing chamber which applies force to the artery. The present invention is an improvement which minimizes effects of motion artifacts on the blood pressure measurement.

In the present invention, the flexible body conformable wall includes a chamber which is separate from the sensing chamber. A first transducer senses pressure within the sensing chamber, while a second transducer senses pressure within the sensing chamber which is a part of the flexible body conformable wall.

The signals from the first and second transducers are processed and used to derive pressure waveform data from which blood pressure values are derived. The use of signals from both the first and the second transducers eliminates fluctuations in the signal from the first transducer which are the result of motion artifacts.

BRIEF DESCRIPTION OF THE DRAWINGS

FIGS. 1A–1D show the detail of the LCD display during a pressure measurement cycle.

FIG. 2 is an electrical block diagram of the blood pressure measuring device of FIG. 1 .

FIG. 6 is a graph illustrating a corrected and scaled waveform taken from the waveforms of FIG. 4.

DETAILED DESCRIPTION

Figure 1:
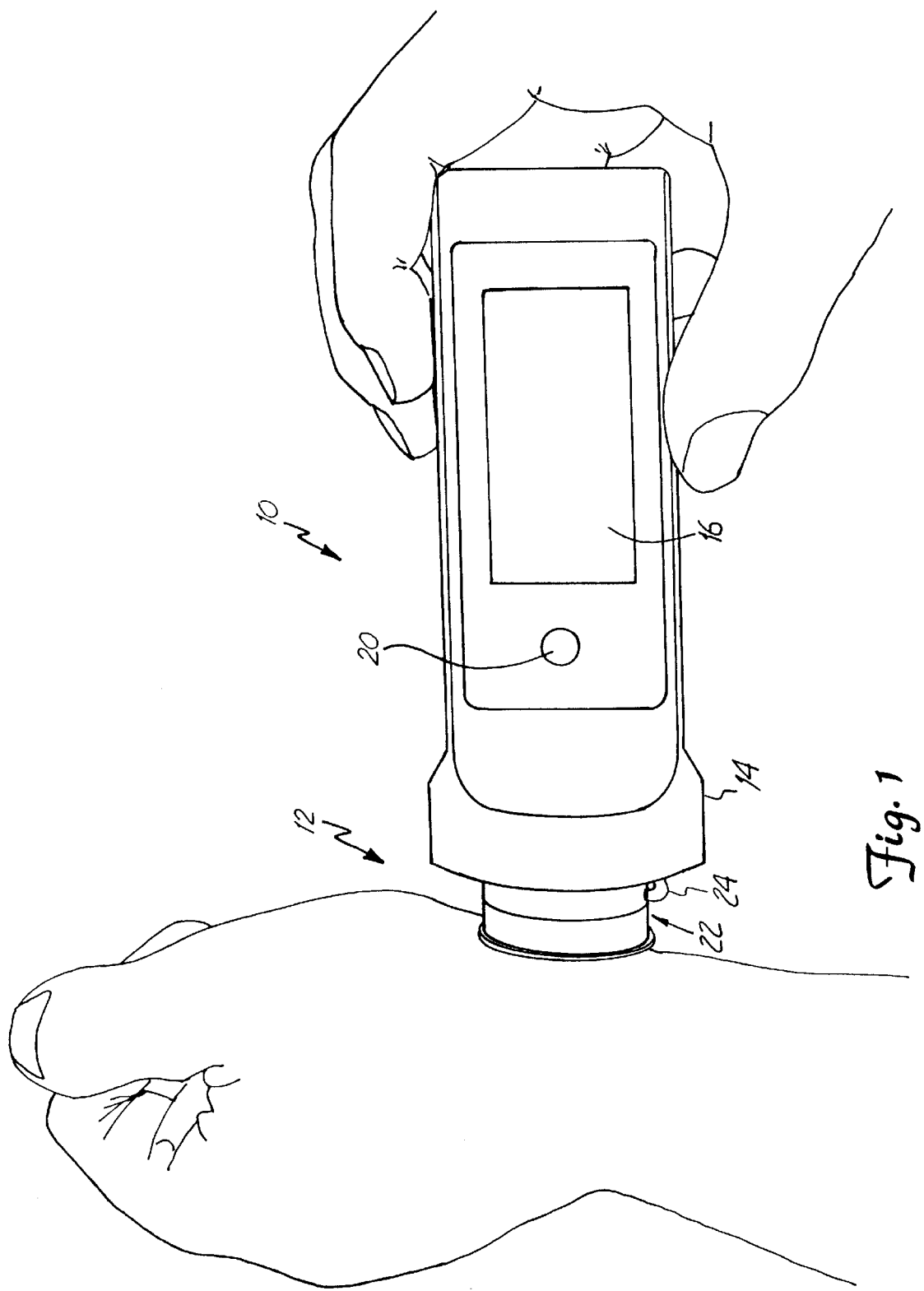
FIG. 1 is a perspective view of a blood pressure measuring device positioned over the wrist of a patient.

FIG. 1 illustrates a hand held blood pressure measurement device being used to measure and display blood pressure within an underlying artery within wrist 12 of a patient. With device 10, a small amount of force is manually applied to the radial artery at the projection of the styloid process bone. As the force is manually applied, blood pressure waveforms are recorded and the corresponding hold down pressure which is being manually applied is also recorded. Using the pressure shape of the blood pressure, waveform parameters are generated. These parameters, along with universal coefficients, are used to calculate pressure values which then can be displayed.

Blood pressure measurement device 10 includes main housing 14, display panel 16, on/off (power) and display select switch 20, sensor interface assembly 22, and connection plug 24.

Housing 14 contains all of the electrical components of measurement device 10. The diameter and length of housing 14 allow it to be easily held by the user (either medical personnel or the patient) during the measurement process. The hold down force is applied by applying force in an axial direction to wrist 12 which is transmitted from housing 14 to sensor interface assembly 22.

Display panel 16 is preferably a liquid crystal display (LCD). In a preferred embodiment, display panel 16 simultaneously displays the following values based upon blood pressure measurements: systolic pressure, diastolic pressure, pulse rate, and mean blood pressure. Display panel 16 also preferably provides visual prompting for manually applying a varying hold down pressure.

Power switch 20 is actuated to turn on power to the circuitry within housing 14. Timing circuitry within housing 14 automatically turns power off after a predetermined period of inactivity. Actuation of switch 20, after the unit is turned on, causes the display to indicate previous readings of blood pressure and pulse rate. In one embodiment there are ten memory locations for readings that can be displayed.

Sensor interface assembly 22 is pivotally mounted to housing 14. As pressure is manually applied by moving housing 14 toward the artery, that force is transferred from housing 14 to sensor interface assembly 22.

In operation, sensor interface assembly 22 is positioned over an artery such as the radial artery (as illustrated in FIG. 1). Alternatively, device 10 can be used in a number of other locations, such as on the temporal artery or the dorsalis pedis artery. The user then begins to apply force to the artery by applying axial force from housing 14 to sensor interface assembly 22. The force applied to the artery is swept in an increasing fashion so that pressure waveform data from a series of pulses are obtained with different amounts of force being applied. To achieve the desired pattern of variable force, user feedback is preferably provided with device 10.

In a preferred embodiment, feedback is in the form of audible tones and/or movable bars on display 16 as shown in FIGS. 1A–1D. Top bar 16A is a pacing bar controlled by the microprocessor. Bottom bar 16B moves in response to the hold down pressure the user applies to the wrist through sensor interface assembly 22. As pressure is applied, bar 16A moves at a fixed rate. The user causes bottom bar 16B to move at approximately the same rate as top bar 16A by applying a steadily increasing force.

The sequence of the measurement cycle is shown in FIGS. 1A–1D. First, the user presses power switch 20, which turns on the device 10. To take a reading, sensor interface assembly 22 is lightly pressed against a pulse locator (as illustrated in FIG. 1) so that bottom bar 16B remains under top bar 16A.

Top bar 16A will start to move across display screen 16. As top bar 16A starts to move, the user must apply increasing pressure through device 10 to the wrist so that bottom bar 16B tracks with the movement of top bar 16A.

Figure 1B:
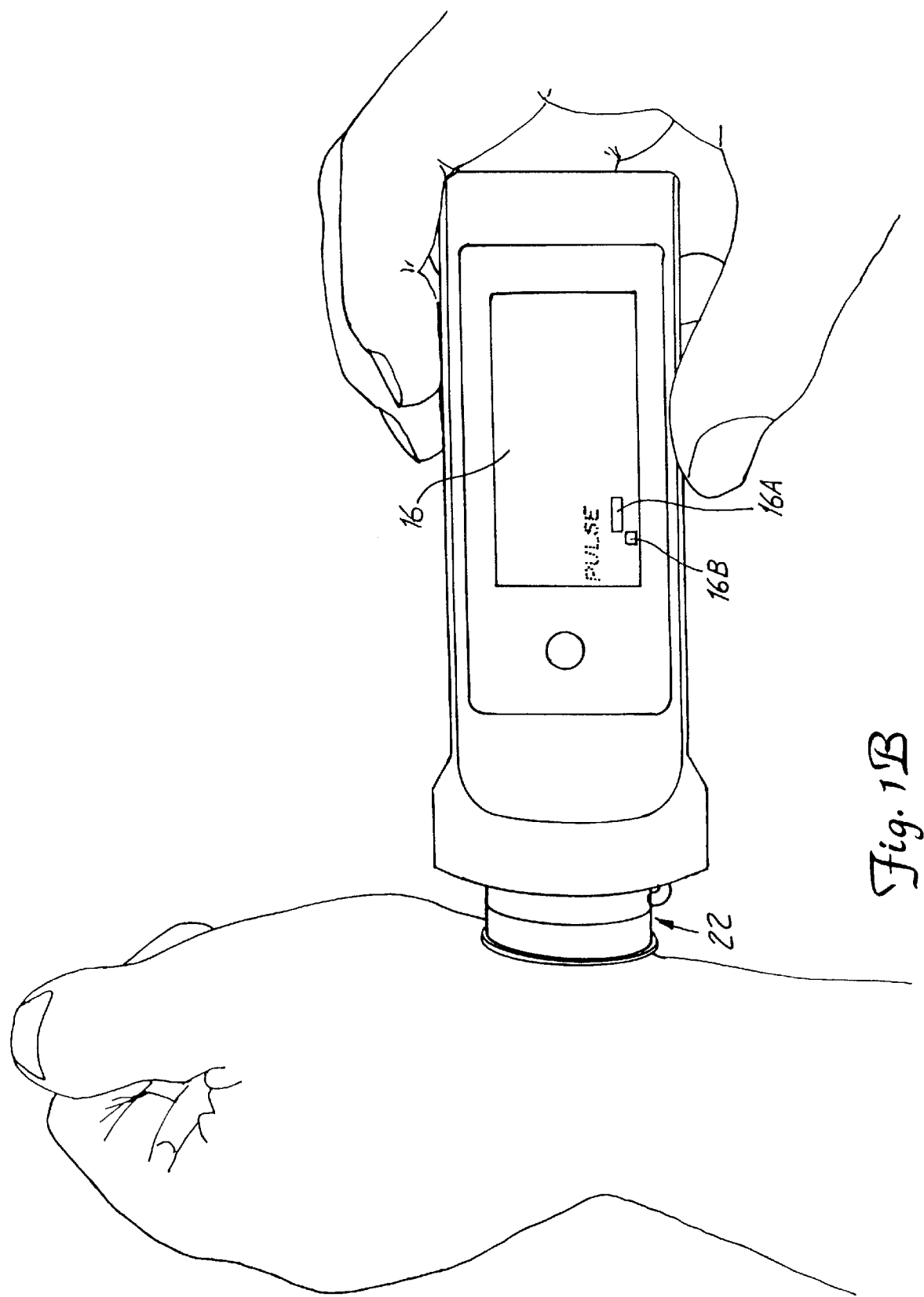

FIG. 1B shows display 16 as top bar 16A has started to move from left to right and bottom bar 16B has not yet begun to track the movement of top bar 16A. FIG. 1C shows bars 16A and 16B as the process continues. Both bars are continuing to move from left to right across the bottom of the display 16. The amount of force required to keep bottom bar 16B underneath top bar 16A will increase as top bar 16A moves across display 16 from left to right.

Figure 1D:
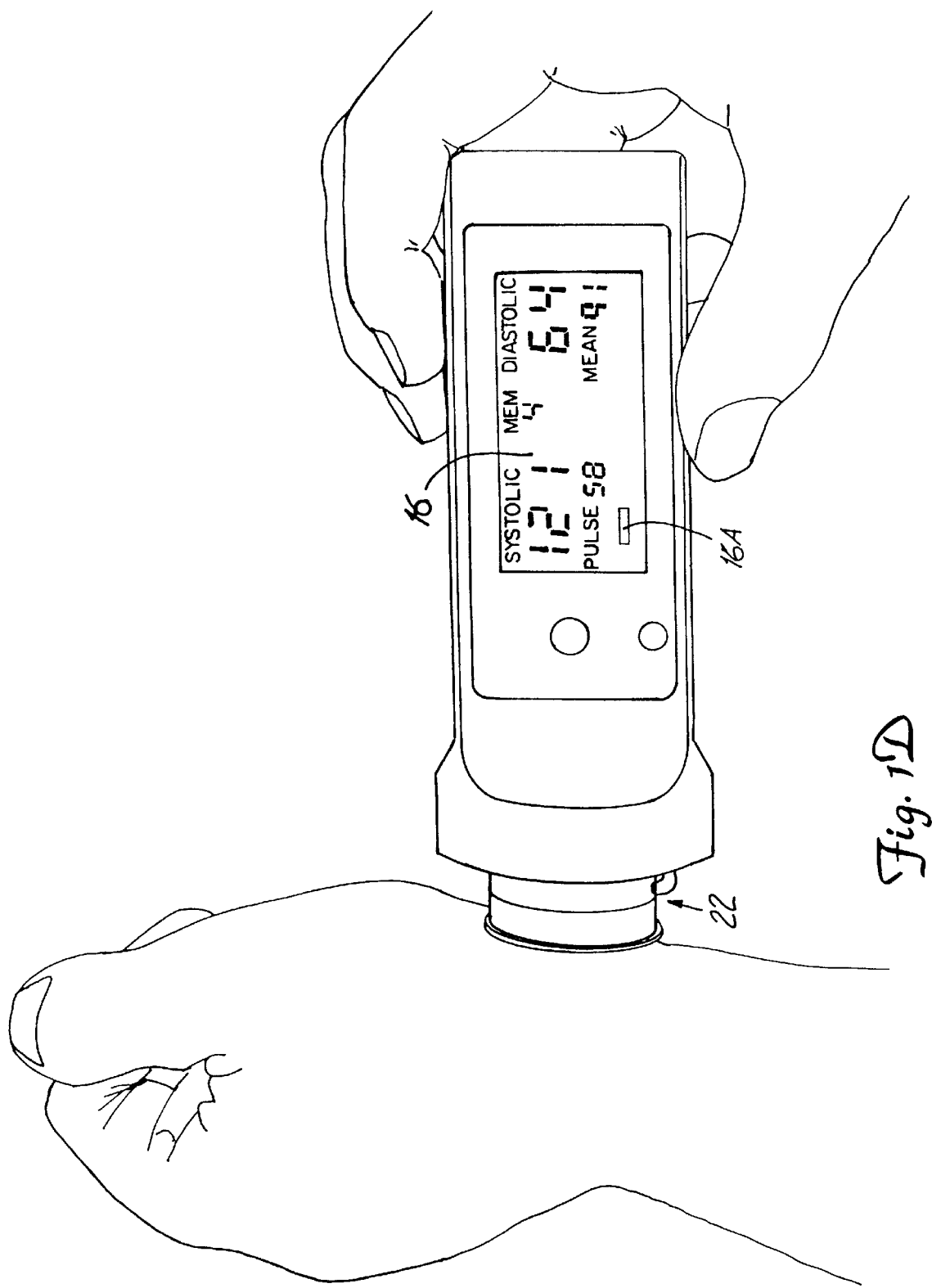

After a beep, the user can remove sensor interface assembly 22 from the wrist. At that point, top bar 16A returns to its left-most position, and bar 16B does not appear on the screen. This is shown in FIG. 1D. The user can then note the blood pressure reading. In a preferred embodiment illustrated in FIG. 1D, display 16 provides a digital readout of systolic, diastolic, and mean blood pressure, as well as pulse rate. An indication of memory location (by number) is also displayed.

As soon as the reading, is complete, device 10 is ready to take another reading. There is no need to clear display 16. Device 10 stores a predetermined number of previous readings (such as the last 10 readings). To review prior readings, power switch 20 is pressed. This causes a different reading from memory to be displayed on display 16.

If a tone method is used as feedback, the user applies a force and each tone is modulated and has a higher pitch sound as the amplitude of the cardiac waveform increases. By listening to the tone, the user knows at what rate to apply the pressure to the artery. At the point of maximum energy transfer between the artery and sensor interface assembly 22, the cardiac pressure waveform reaches a peak amplitude and, therefore, the highest frequency tone is produced. As the user continues to apply higher pressure to the artery, the amplitude of the cardiac pressure waveform decreases, and therefore the frequency of the tone decreases. By listening to the tone, the user can perform a variable pressure sweep to measure pressure using device 10.

Feedback to the user can be supplied in other ways as well. For example, an audible tone can be produced using a combination of frequency modulation and amplitude modulation. In other words, as the amplitude of the pressure waveform increases, both pitch (frequency) and amplitude (volume or loudness) of the tone will change.

FIG. 2 is a electrical block diagram of device 10. Pressure transducers 26A and 26B and nonvolatile memory 28 within sensor interface assembly 22 are connected through connector 30 and connector 24 to circuitry within housing 14. Power supply circuit 31 includes switch 20, OR circuit 32, delay circuit 33, battery 34, reverse battery protection 35, integrated power switch 36, analog regulator 37, and voltage dividers 38A and 38D. The output of analog regulator 37 is electrical power which is used to energize analog circuitry, which includes amplifiers 40A and 40B, and analog-to-digital (A/D) converter 42. Integrated power switch 36 supplies power to all digital circuits, which include microprocessor 44, speaker 46, display panel 16 and associated display drive and memory circuitry 48. Microprocessor 44 includes digital signal processing circuitry 50, read only memory (ROM) and electrically erasable programmable read only memory (EEPROM) 52, random access memory (RAM) 54, timer circuitry 56, and input/output ports 58. A/D converter 42 may be integrated with microprocessor 44, while some of the memory may be external to microprocessor 44.

Switch 20 is partially a monitoring pushbutton switch. Pressing switch 20 causes OR circuit 32 to turn on integrated power switch 36. Integrated power switch 36 supplies power to microprocessor 44, which in turn latches on OR circuit 32. The turn off of the circuit is controlled by microprocessor 44 discontinuing a signal to OR circuit 32. This occurs through a fixed time of no activity.

Transducers 26A and 26B sense pressure communicated within sensor interface assembly 22 and supply electrical signals to connector 30. In a preferred embodiment, transducers 26A and 26B are piezoresistive pressure transducers. Nonvolatile memory 28 stores offsets of transducers 26A and 26B and other information such as sensor serial number. Nonvolatile memory 28 is, in a preferred embodiment, an EEPROM.

The outputs of transducers 26A and 26B are analog electrical signals representative of sensed pressure. These signals are amplified by amplifiers 40A and 40B and applied to inputs of A/D converter 42. The analog signals to A/D convertor 42 are converted to digital data and supplied to the digital signal processing circuitry 50 of microprocessor 44.

Based upon the pressure data received, microprocessor 44 performs calculations to determine blood pressure values. Those calculations will be described in more detail later. As each pulse produces a cardiac waveform, microprocessor 44 determines a peak amplitude of the waveform. Microprocessor 44 controls display driver 48 to create bars 16A and 16B of FIGS. 1A–1D or drives speaker 46 to produce audible tones which vary as a function of the hold down pressure. The moving bars or audible tones guide the user in applying a variable force to the artery.

When a measurement cycle has been completed, microprocessor 44 reorders the cardiac waveforms in increasing order of their corresponding hold down pressure and performs calculations to determine systolic pressure, diastolic pressure, mean blood pressure, and pulse rate. These values are displayed as shown in FIG. 1D. If switch 20 is pressed while microprocessor 44 is on, a signal is supplied through delay circuit 33 to microprocessor 44, causing it to toggle to a new pressure reading. The memory location of that pressure reading is also displayed, as shown in FIG. 1D.

Figure 3A:
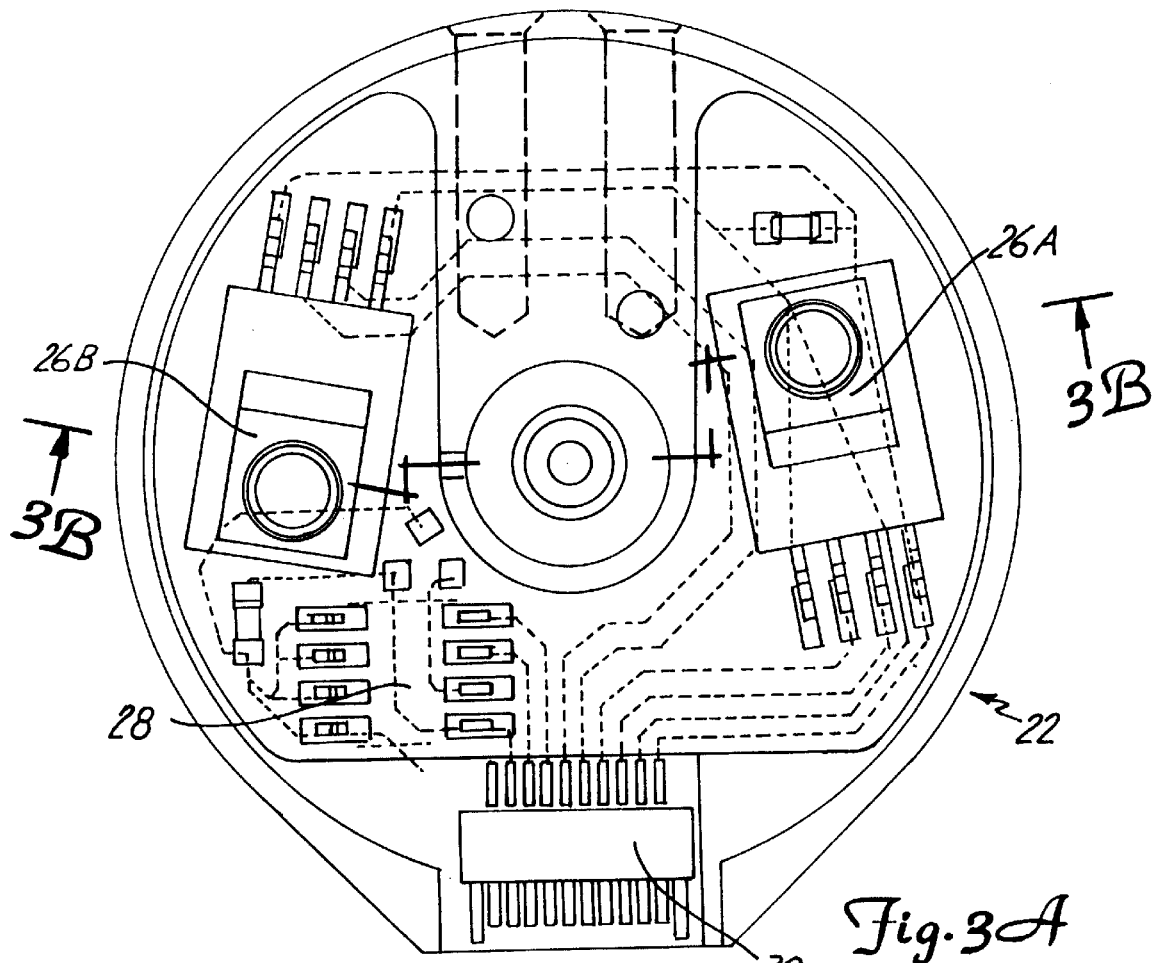
FIG. 3A is a top view of the sensor interface assembly.
Figure 3B:
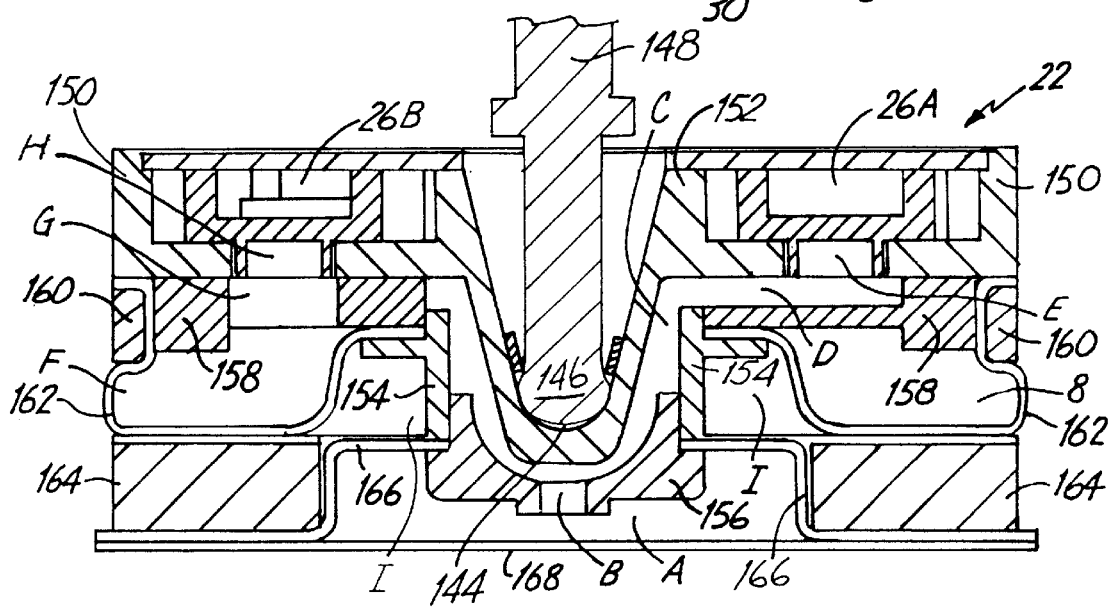
FIG. 3B is a cross-sectional view of the sensor interface assembly along section 3B—3B of FIG. 3A.

FIGS. 3A and 3B illustrate sensor interface assembly 22 in detail. Sensor interface assembly 22 includes top plate 150, upper cup 152, upper capture 154, diaphragm capture 156, inner mounting ring 158, outer mounting ring 160, side wall diaphragm 162, damping ring 164, inner diaphragm 166, and outer diaphragm 168.

As shown in FIG. 3B, transducer 26A measures fluid pressure in fluid-filled sensor chamber A. Channels B, C, D, and E provide fluid pressure communications between transducer 26A and sensor chamber A. Transducer 26B measures fluid pressure in fluid-filled ring chamber F. Channels G and H provide fluid pressure communications between transducer 26B and ring chamber F. Connector 30 communicates with transducers 26A and 26B and non-volatile memory 28.

FIG. 3B also shows how the sensor interface assembly 22 is pivotally connected to housing 14 by a ball 146 and socket 144 arrangement. The ball 146 is pivotally mounted in socket 144. Ball 146 is pivotally mounted in socket 144. Because sensor interface assembly 22 is pivotally coupled to stem 148 about a low pivot point. This permits sensor interface assembly 22 to be stably positioned above the underlying artery. In addition, the low pivot point enables the user to apply a more direct, uniform force on outer diaphragm 168. Thus, the hold down pressure manually applied by the user (through housing 14 and stem 148) is more uniformly applied to the anatomy above the underlying artery.

Side wall diaphragm 162 and rings 158 and 160 define annular deformable ring chamber F coupled to ring 164. Side wall diaphragm 162 is preferably formed from a generally circular sheet of flexible material, such as polyurethane, and is filled with fluid. Diaphragm 162 has a hole sized to fit around the upper portion of upper capture 154. The outer edge portion of diaphragm 162 is trapped and held between outer ring 160 and top plate 150. The inner edge portion of diaphragm 162 is trapped and supported between ring 158 and upper capture 154. Diaphragm 162 is made from a flexible material and is bulged outward when ring chamber F is filled with fluid. Ring chamber F is compressible and expandable in the vertical direction so as to be able to conform to the anatomy of the patient surrounding the underlying artery. As a result, the distance between top plate 150 and the patient's anatomy can vary around the periphery of side wall diaphragm 162 according to the contour of the patient's anatomy. Furthermore, because fluid is permitted to flow through and around chamber F, pressure is equalized around the patient's anatomy.

Damping ring 164 generally consists of an annular compressible ring and is preferably formed from a foam rubber or other pulse dampening material such as open celled foam or closed cell foam. Ring 164 is centered about and positioned between side wall diaphragm 162 and diaphragms 166 and 168. Damping ring 164 is isolated from the fluid coupling medium within sensor chamber A. Because ring 164 is formed from a compressible material, ring 164 absorbs and dampens forces in a direction parallel to the underlying artery which are exerted by the blood pressure pulses on sensor interface assembly 22 as the blood pressure pulse crosses sensor interface assembly 22. Because bottom ring 164 is isolated from the fluid coupling medium in sensor chamber A, the forces absorbed or received by ring 164 cannot be transmitted to the fluid coupling medium. Instead, these forces are transmitted across ring 164 and side wall diaphragm 162 to top plate 150. Because this path is distinct and separate from the fluid coupling medium, sensor chamber A and the fluid coupling medium are isolated from these forces. In addition, ring 164 also presses tissue surrounding the artery to neutralize or offset forces exerted by the tissue.

Upper diaphragm 166 is an annular sheet of flexible material having an inner diameter sized to fit around diaphragm capture 156. An inner portion of upper diaphragm 166 is trapped or captured (and preferably adhesively affixed) between the lip of diaphragm capture 156 and the bottom rim of upper capture 154.

The intermediate portion of upper diaphragm 166 is adjacent to expansion cavity I and is isolated from ring 164 and ring chamber F. Upper diaphragm 166 is permitted to initially move upward into expansion cavity I as ring chamber F, ring 164, and outer diaphragm 168 conform to the anatomy of the patient surrounding the underlying artery. As ring 164 is pressed against the anatomy of the patient surrounding the artery to neutralize or offset forces exerted by the tissue, outer diaphragm 168 is also pressed against the anatomy and the artery. However, because upper diaphragm 166 is permitted to roll into expansion cavity I, sensor chamber A does not experience a large volume decrease and a large corresponding pressure increase. Thus, sensor interface assembly 22 permits greater force to be applied to the anatomy of the patient through ring 164 to neutralize tissue surrounding the artery without causing a corresponding large change in pressure within sensor chamber A as the height of the side wall changes. As a result, sensor interface assembly 22 achieves more consistent and accurate blood pressure measurements.

Outer diaphragm 168 is a generally circular sheet of flexible material capable of transmitting forces from an outer surface to fluid within sensor chamber A. Outer diaphragm 168 is coupled to inner diaphragm 166 and is configured for being positioned over the anatomy of the patient above the underlying artery. Outer diaphragm sheet 168 includes nonactive portion or skirt and an active central portion. The skirt constitutes the area of diaphragm 168 where inner diaphragm 166 is heat sealed or bonded to outer diaphragm 168.

The active portion of outer diaphragm 168 is not bonded to inner diaphragm 166, and is positioned below and within the inner diameter of ring 164.

The active portion of outer diaphragm 168 is the active area of sensor interface assembly 22 which receives and transmits pulse pressure to transducer 26A.

The coupling medium within sensor chamber A and passages B–E may consist of any fluid (gas or liquid) capable of transmitting pressure from diaphragm 168 to transducer 26A. The fluid coupling medium interfaces between the active portion of outer diaphragm 168 and transducer 26A to transmit blood pressure pulses to transducer 26A. Because the fluid coupling medium is contained within sensor chamber A and passages B–E, which are isolated from the side wall of sensor interface assembly 22, the fluid coupling medium does not transmit blood pressure pulses parallel to the underlying artery, forces from the tissue surrunding the underlying artery and other forces absorbed by the side wall to transducer 26A. Forces parallel to the underlying artery are dampened by the compressible material of ring 164. As a result, sensor interface assembly 22 more accurately measures and detects arterial blood pressure.

Sensor interface assembly 22 provides external measurements of blood pressure in an underlying artery. Because sensor interface assembly 22 senses blood pressure non-invasively, blood pressure is measured at a lower cost and without medical risks. Because sensor interface assembly 22 is relatively small compared to the larger cuffs used with oscillometric and auscultatory methods, sensor interface assembly 22 applies a hold down pressure to only a relatively small area above the underlying artery of the patient. Consequently, blood pressure measurements may be taken with less discomfort to the patient. Because sensor interface assembly 22 does not require inflation or deflation, faster, more frequent measurements may be taken.

Furthermore, sensor interface assembly 22 better conforms to the anatomy of the patient so as to be more comfortable to the patient and so as to achieve more consistent and accurate blood pressure measurements. Because ringy chamber F is deformable and filled with fluid, ring chamber F better conforms to the anatomy of the patient and equalizes pressure applied to the patient's anatomy. Because ring 164 is compressible and because outer diaphragm 168 is flexible and is permitted to bow or deform inwardly, ring 164 and outer diaphragm 168 also better conform to the anatomy of the patient. At the same time, however, sensor interface assembly 22 does not experience a large sudden increase in pressure in sensor chamber A as ring 164 and outer diaphragm 168 are pressed against the anatomy of the patient. Ring chamber F and ring 164 apply force to the anatomy of the patient to neutralize the forces exerted by tissue surrounding the underlying artery. Because ring chamber F and ring 164 are both compressible in height, the height of the side wall decreases as the side wall is pressed against the patient. Diaphragms 166 and 168 are also conformable. However, because the intermediate portion of inner diaphragm 166 is permitted to move upward into expansion cavity I, sensor chamber A does not experience a large volume decrease and a corresponding large pressure increase. Thus, the side wall is able to apply a greater force to the anatomy of the patient without causing a corresponding large, error-producing increase in pressure within sensor chamber A due to the change in height of the side wall and the change in shape of outer diaphragm 168.

At the same time, sensor interface assembly 22 permits accurate and consistent calculation of blood pressure. Because of the large sensing area through which blood pressure pulses may be transmitted to transducer 26A, sensor interface assembly 22 is not as dependent upon accurate positioning of the active portion of outer diaphragm 168 over the underlying artery. Thus, sensor interface assembly 22 is more tolerant to patient movement as measurements are being taken.

Moreover, sensor interface assembly 22 achieves a zero pressure gradient across the active face of the sensor, achieves a zero pressure gradient between the transducer and the underlying artery, attenuates or dampens pressure pulses that are parallel to the sensing surface of the sensor, and neutralizes forces of the tissue surrounding the underlying artery. Sensor interface assembly 22 contacts and applies force to the anatomy of the patient across the skirt and the active portion of outer diaphragm 168. However, the pressure within sensor chamber A is substantially equal to the pressure applied across the active portion of outer diaphragm 168. The remaining force applied by sensor interface assembly 22 across the skirt, which neutralizes or offsets forces exerted by the tissue surrounding the underlying artery, is transferred through the side wall (ring 164 and ring chamber F) to top plate 150. As a result, the geometry and construction of sensor interface assembly 22 provides the proper ratio of pressures between the skirt and the active portion of outer diaphragm 168 to neutralize tissue surrounding the underlying artery and to accurately measure the blood pressure of the artery. In addition, because the fluid coupling medium within sensor chamber A is isolated from the side wall, pressure pulses parallel to the underlying artery, forces from tissue surrounding the underlying artery, and other forces absorbed by the side wall are not transmitted through the fluid coupling medium to transducer 26A. Consequently, sensor interface assembly 22 also achieves a zero pressure gradient between transducer 26A and the underlying artery.

Blood pressure measuring device 10 determines blood pressure values from the sensed waveform pressure amplitudes sensed by sensor interface assembly 22 and from other parameters derived from the pressure amplitudes using a stored set of coefficients. A pressure amplitude is determined at each sample point.

Device 10 calculates a systolic blood pressure value (S), a mean blood pressure value (M) and a diastolic blood pressure value (D) based upon the following formulas:

$$M = F_m(P_1^m, \ldots, P_n^m, C_1^m, \ldots, C_n^m)$$

$$S = F_s(P_1^s, \ldots, P_n^s, C_1^s, \ldots, C_n^s)$$

$$D = F_d(P_1^d, \ldots, P_n^d, C_1^d, \ldots, C_n^d)$$

wherein $F_m$, $F_s$, $F_d$ are linear or non-linear functions, $P_1^m$, $P_1^s$, $P_1^d$, ..., $P_n^m$, $P_n^s$, $P_n^d$ are parameters derived from waveform pressure amplitudes, and $C_1^m$, $C_1^s$, $C_1^d$, ..., $C_n^m$, $C_n^s$, $C_n^d$ are coefficients obtained during training processes based upon clinical data.

In particular, device 10 calculates a systolic blood pressure value (S), a mean blood pressure value (M), a diastolic blood pressure value (D) based upon the following formulas:

$$M = C_1^m P_1^m + C_2^m P_2^m + \ldots + C_n^m P_n^m$$

$$S = C_1^s P_1^s + C_2^s P_2^s + \ldots + C_n^s P_n^s$$

$$D = C_1^d P_1^d + C_2^d P_2^d + \ldots + C_n^d P_n^d$$

wherein $P_1^m$, $P_1^s$, $P_1^d$ ... $P_n^m$, $P_n^s$, $P_n^d$ are parameters derived from waveform pressure amplitudes. Such parameters may be calculated from shape characteristics of the waveform or parameters calculated from fuinctions such as curves based upon relationships between particular points of several waveforms. The parameters may be further based upon hold down pressure values and time periods between particular points on the waveforms. The values cam, $C_1^m$, $C_1^s$, $C_1^d$ ... $C_n^m$, $C_n^s$, $C_n^d$ are coefficients obtained during training processes based upon clinical data.

In addition, the pulse rate (PR) may also be determined using the formula:

$$PR = \frac{PR_1 + PR_2 + PR_3 + PR_4}{4}$$

To determine the pulse rate, four individual waveforms, or beats, are sensed and are time averaged to determine the pulse rate. Preferably, the waveforms used to determine pulse rates include the waveform having the largest maximum pressure amplitude, the two waveforms prior to the waveform having the largest maximum pressure amplitude and the waveform succeeding the waveform having the largest maximum pressure amplitude. Once the four waveforms are identified, the pulse rate of each waveform is determined. The sum of the pulse rate of the four waveforms is then divided by four to calculate pulse rate PR. The pulse rate (PR) for each waveform is based upon the following formula:

$$PR_N \text{ beats per minute } (N = 1, 2, 3, 4) = \frac{128 \text{ samples/sec}}{\text{No. samples/beat}_N} \times 60 \text{ sec/min}$$

Figure 4:
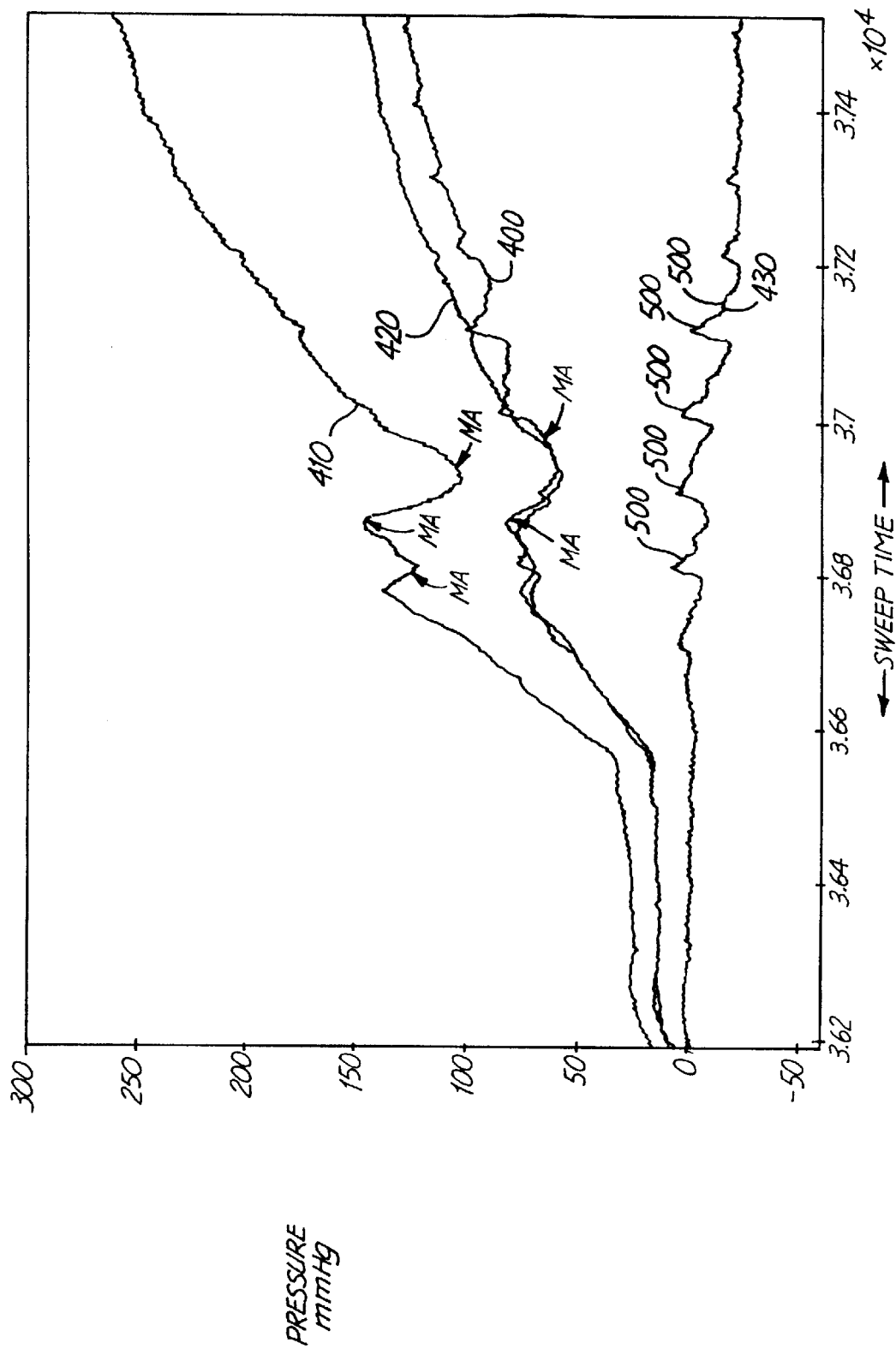
FIG. 4 is a graph illustrating blood pressure waveforms.
Figure 5:
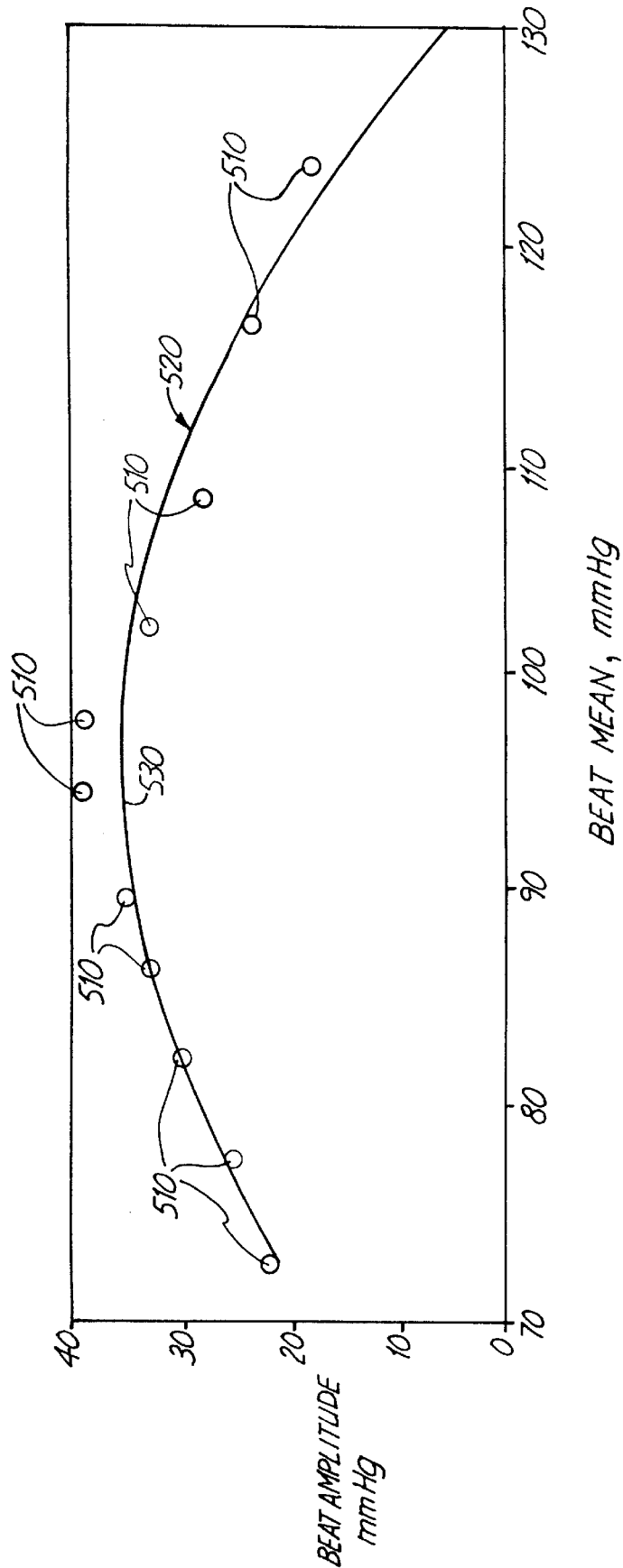
FIG. 5 is a graph illustrating a curve fit from points taken from the waveforms of FIG. 4.

FIGS. 4, 5, and 6 illustrate representative parameters which may be used to calculate blood pressure values. FIG. 4 illustrates a sample series of waveforms exhibited by the underlying artery as a varying pressure is applied over time. The vertical scale indicates pressure in mmHg while the horizontal scale indicates individual sample points at which the blood pressure values exerted by the pulse are measured over time. In the preferred embodiment, transducers 26A and 26B produce continuous electrical signals representing waveform pressures which are sampled 128 times per second.

In the preferred embodiment, the hold down pressure applied to sensor interface assembly 22 is swept over a preselected range of increasing hold down pressures. Preferably, the sweep range of hold down pressures typically is begun at approximately 20 mmHg. The hold down pressure is then steadily increased (under the prompting or guidance from the audible or visual feedback) until two individual waveforms are sensed following the sensed waveform having the largest pressure amplitude. Preferably, each sweep range extends between an initial hold down pressure of about 20 mmHg and a final hold down pressure of approximately 150% of the mean hold down pressure of the waveform having the largest maximum pressure amplitude during the previous sweep.

FIG. 4 shows the signals 400 and 410 from transducers 26A and 26B, respectively, as sensor interface assembly 22 is pressed against the artery. Signal 400 is representative of pressure in sensor chamber A. Signal 410 represents the pressure in ring chamber F as sensed by transducer 26B. Signal 420 is representative of pressure in ring chamber F after by applying a proper gain and offset signal 410 is calibrated to match signal 400. This gain and offset adjustment can take place in an initial phase of a pressure measurement. This gain and offset adjustment can also take place on a continual basis or at any other phase of a pressure sweep. A least square fit can be used to find the best fit of curves 400 and 420 so as to get the best gain and offset adjustment.

At multiple places during the sweep, signals 400 and 420 are affected by patient movement or (in the case of a hand-held blood pressure unit) operator movement as the sweep is performed. These inflections or motion artifacts MA show noise that needs to be taken out of the system in order to measure blood pressure. Signal 430 has most of the noise taken out of signal 400. Signal 430 contains pressure pulse waveforms 500 from the movement of the arterial walls as sensor interface assembly 22 pressed against the arterial wall.

Signal 430 can be derived by subtracting signal 420 from signal 400. Signal 430 represents blood pressure pulses that can be used to obtain shape and amplitude information to calculate blood pressure. Signal 400 can be used to obtain additional information such as hold down pressure that is also used to calculate pressure. The process of calculating pressure using shape, amplitude, and hold down is described in the previously mentioned Medwave patents and patent application, which are incorporated by reference, and is also described in the following description.

As can be observed in FIG. 4, when noise causes signal 400 to sweep in a non-uniform movement, it may be required to reorder the beats in order of increasing hold down pressure in order to calculate blood pressure.

Based upon sensed and sampled pressure waveform signals or data produced by transducers 26A and 26B during each sweep of hold down pressures, microprocessor 44 derives preselected parameters for calculating blood pressure values from the derived parameters and a stored set of coefficients. As indicated in FIG. 4, parameters may be derived directly from the absolute waveform pressures which vary as hold down pressure is varied over time. Such parameters may be derived from the shape of the waveforms including a particular waveform's slope, absolute pressure at a selected sample point, a rise time to a selected sample point on a waveform, and the hold down pressures corresponding to a particular sample point on a waveform. As can be appreciated, any of a variety of parameters may be derived from the absolute waveform pressures shown in FIG. 4. Parameters may further be based upon particular points or functions of the sample points.

FIG. 5 illustrates an example of how values or parameters of multiple waveforms 500 shown in FIG. 4 may be used to derive additional parameters. FIG. 5 shows several data points 510. Each data point 510 represents a selected waveform 500 taken from signal 430 and the corresponding hold down pressure of waveform 400 both shown in FIG. 4. Curve 520 is derived by fitting points 510 to a preselected function or relationship. Parameters such as the peak 530 are then derived from curve 520. As can be appreciated, various other parameters such as slope may also be derived from curve 520. Parameters derived from curve 520 are ultimately based upon pressure waveforms 500 and 400 shown in FIG. 4 which are produced from sensed pressure waveform data or signals from transducers 26A and 26B. However, because curve 520 is derived using a plurality of waveforms, parameters derived from curve 520 represent the overall relationship between the plurality of waveforms. In other words, parameters derived from curve 520 represent the way in which the plurality of waveforms (shown in FIG. 4) are related to one another. Data points 510 represent corrected, relative waveform pressures. As can be appreciated, functions such as curves may also be derived using absolute waveform pressure values which are shown in FIG. 4.

A waveform is "corrected" by subtracting from the hold down pressure 400 curve 420, which is the ring pressure 410 corrected by a gain and offset. Correcting a waveform eliminates characteristics of the waveform which result from a continuously increasing hold down pressure being applied to the artery during each waveform or cardiac cycle.

In the application of device 10, the user may not apply a linear increase of pressure. Device 10 records the amplitude and hold down pressure. Even if these beats are recorded out of sequence, i.e. a beat with a corresponding higher hold down pressure is recorded before a beat with a low hold down pressure, microprocessor 44 can still generate a curve (such as curve 520 of FIG. 5) as long as there are several beats recorded over the pressure range. With this information recorded, microprocessor 44 can generate the required parameters and calculate pressure.

FIG. 6 further illustrates other parameters which may be derived from waveform pressure values as shown in FIG. 4. FIG. 6 illustrates a waveform 600 selected from waveforms 500. Waveform 600 is preferably the waveform having the largest peak or maximum pressure amplitude. Alternatively, waveform 600 may be any of the waveforms 500 (shown in FIG. 4) such as waveforms immediately preceding or succeeding the waveform having the largest maximum pressure amplitude. As shown in FIG. 6, waveform 600 is corrected such that the beginning point 602 and an ending point 604 have the same absolute waveform pressure value. As further shown by FIG. 6, waveform 600 is horizontally and vertically scaled to eliminate gain from parameters derived from waveform 600. Preferably, waveform 600 is scaled from zero to twenty-one beginning at beginning point 602 and ending at ending point 604 of waveform 600 on the horizontal b axis. Preferably, waveform 600 is vertically scaled from zero to one beginning at its base and ending at its peak. Because waveform 600 is horizontally and vertically scaled, parameters may be derived from waveform 600 for calculating blood pressure values without the gain of the particular patient affecting the calculated blood pressure value. Gains are caused by the differences between the actual pressure exerted within the artery and the pressures sensed at the surface of the wrist or anatomy which is caused by varying characteristics of the intermediate tissue. Scaling waveform 600 eliminates any gains exhibited by individual patients. By using scaled values to locate corresponding points or waveform pressure amplitudes on waveform 600, points on waveform 600 uniformly correspond to the same points on waveforms exhibited by other patients.

As shown by FIG. 6, various parameters may be derived from scaled, corrected waveform 600. As shown by FIG. 6, such parameters include widths of waveform 600 at selected points along the vertical y axis, ratios of individual waveform pressure amplitudes at selected points along the horizontal b axis and the amplitude of the waveform, the rise time, or time elapsed from the start of waveform 600 at point 602 to a selected point along the vertical y axis. In addition, several other parameters may also be derived from waveform 600, such as slope and other shape characteristics.

Once the parameters to be used in calculating blood pressure values are selected, coefficients corresponding to each parameter may be used to calculate blood pressure. Coefficients represent the relationship between a particular parameter set and the resulting blood pressure value to be determined from a particular parameter set. Coefficients are ascertained from clinical tests upon patients having known blood pressure values. Typically, the known blood pressure value is determined using the A-line method which is generally accurate, although difficult to set up, expensive and medically risky. As the blood pressure is determined using the A-line or other methods, sensor interface assembly 22 is positioned over the underlying artery of the patient. A varying pressure is applied to the artery of the patient having the known blood pressure value. As discussed above, transducer 26A produces sensed pressure waveform signals or data representing arterial pressure waveforms. Microprocessor 44 receives the produced sensed pressure waveform data and derives preselected parameters from the sensed pressure waveform data. Coefficients are then determined using the derived values of the selected parameters and the known blood pressure value. Each coefficient corresponding to each selected parameter is a function of the known blood pressure values and the derived parameters. Preferably, several patients are clinically tested to ascertain the coefficients. Once obtained, the coefficients are stored for use in non-invasively calculating blood pressure values of other patients without the necessity of using the more time consuming, expensive and risky A-line method and without using the generally more inaccurate conventional blood pressure measuring methods. Each particular coefficient is preferably ascertained so as to be applicable for calculating blood pressure values from the derived waveform parameters of all patients. Alternatively, individualized coefficients may be used to calculate blood pressure values from derived waveform parameters of particular patients falling within a particular age group or other specialized groups.

In addition to illustrating various methods by which parameters may be derived from waveform pressure data, FIGS. 4, 5, and 6 illustrate particular parameters for use in calculating a systolic, a mean and a diastolic blood pressure value of a particular patient during an individual hold down pressure sweep. According to the preferred method of the present invention, a sweeping, continuously varying hold down pressure is applied to the underlying artery. Preferably, the hold down pressure applied during each sweep begins at about 20 mmHg and ramps upward over time until at least two waveforms are detected by transducer 26A after the waveform having the largest maximum pressure is identified. Based upon the produced sensed pressure waveform data representing the waveforms as representatively shown by FIG. 4, microprocessor 44 calculates systolic, mean, and diastolic blood pressure using a stored set of coefficients. Systolic blood pressure (S) is calculated using the formula:

$$S = C_1^s P_1^s + C_2^s P_2^s + C_3^s P_3^s + C_4^s P_4^s + C_5^s P_5^s + C_6^s P_6^s + C_7^s P_7^s + C_8^s P_8^s + C_9^s$$

Coefficients $C_1^s$–$C_9^s$ are stored coefficients ascertained according to the earlier described method of the present invention. $C_9^s$ is an offset value. Parameters $P_1^s$ and $P_2^s$ are derived from relative waveform pressure amplitudes corresponding to scaled values taken from a scaled and corrected beat as represented by waveform 600 in FIG. 6. Preferably, parameter $P_1^s$ is the ratio defined by the waveform pressure amplitude on 20 waveform 600 which corresponds to scale value $b_1$ along the horizontal axis divided by the maximum waveform pressure amplitude or peak (point 606) of waveform 600. Parameter $P_2^s$ preferably is the ratio defined by the waveform pressure amplitude of point 608 on waveform 600 that corresponds to scale value $b_3$ along the horizontal $b_3$ axis divided by the maximum waveform pressure amplitude or peak (point 606) of waveform 600.

Parameter $P_3^s$ is preferably the rise time or the time elapsed from the start of the waveform to a particular point along waveform 600 corresponding to a particular vertical scale value. Preferably, parameter $P_3^s$ is the elapsed time from the start of waveform 600 to a point 610 on waveform 600 which has a vertical height of approximately 0.18 that of a maximum pressure amplitude or peak (point 606) of waveform 600. This rise time or elapsed time is represented as 612 in FIG. 6.

Parameter $P_4^s$ is the mean pressure of the uncorrected waveform 500 (shown in FIG. 4) having the highest peak or maximum pressure. Parameter $P_5^s$ is the systolic point of the uncorrected pressure waveform immediately following the uncorrected pressure waveform having the largest maximum pressure.

Parameter $P_6^s$ is a parameter taken from a function such as a curve derived from values of a plurality of waveforms 500 (shown in FIG. 4). Preferably, parameter $P_6^s$ is the peak pressure of curve 520 shown in FIG. 5. The peak is represented by point 530. Curve 520 is preferably generated by fitting the relative waveform pressure amplitude of waveforms 500 (shown in FIG. 4) to the function or mathematical expression of:

$$\text{AMPLITUDE} = \exp(ax^2 + bx + c),$$

wherein x=the mean pressure amplitude of each pressure waveform.

Parameter $P_7^s$ is a time value representing a width of waveform 600 (represented by segment 614 between points 616 and 618) which corresponds to a selected percentage of the maximum pressure amplitude or peak (point 606) of waveform 600. The time elapsed between points 616 and 618 is determined by counting the number of samples which lie above points 616 and 618 on waveform 600. Preferably, parameter $P_7^s$ is the width of waveform 600 at a height of about 0.9 A, where A is the maximum waveform pressure amplitude of waveform 600 (point 606).

Parameter $P_8^s$ is the maximum slope of the uncorrected waveform 500 immediately following the waveform 500 having the largest maximum pressure or peak.

The mean blood pressure value (M) is calculated using the formula:

$$M = C_1^m P_1^m + C_2^m P_2^m + C_3^m P_3^m + C_4^m P_4^m + C_5^m$$

Coefficients $C_1^m$–$C_5^m$ are stored coefficients ascertained according to the earlier described method of the present invention. Coefficient $C_5^m$ is an offset. Parameters $P_1^m$ and $P_2^m$ are derived from relative waveform pressure amplitudes corresponding to scaled values taken from the scaled and corrected beat as represented by waveform 600 in FIG. 6. Preferably, parameter $P_1^m$ is the ratio defined by the waveform pressure (point 620) on waveform 600 which corresponds to the scale value $b_9$ along the horizontal axis divided by the maximum waveform pressure amplitude or peak (point 606) of waveform 600. Similarly, parameter $P_2^m$ is the ratio defined by the waveform pressure on waveform 600 which corresponds to scale value $b_{13}$ along the horizontal axis (point 622) divided by the maximum waveform pressure amplitude or peak (point 606) of waveform 600.

Parameter $P_3^m$ is identical to parameter $P_4^s$ used to calculate systolic blood pressure. Parameter $P_4^m$ is identical to parameter $P_6^s$ used to calculate systolic blood pressure.

Diastolic blood pressure values (D) are calculated using the formula:

$$D = C_1^d P_1^d + C_2^d P_2^d + C_3^d P_3^d + C_4^d P_4^d + C_5^d P_5^d + C_6^d P_6^d + C_7^d P_7^d + C_8^d$$

Coefficients $C_1^d$–$C_8^d$ are stored coefficients ascertained according to the earlier described method of the present invention. Coefficient $C_8^d$ is an offset value. Parameter $P_1^d$ is derived from relative waveform pressure corresponding to scaled values taken from a scaled and corrected beat as represented by waveform 600 in FIG. 6. Preferably, parameter $P_1^d$ is a ratio defined by the waveform pressure amplitude on waveform 600 which corresponds to scale value $b_{12}$ along the horizontal axis (point 624) divided by the maximum waveform pressure amplitude or peak (point 606) of waveform 600.

Parameter $P_2^d$ is identical to parameter $P_3^s$ used to calculate the systolic blood pressure. Preferably, parameter $P_3^d$ is the width of segment 626 between points 628 and 630. Preferably points 626 and 628 are points along waveform 600 that are located at a height of 0.875 A, where A is the maximum pressure amplitude (point 606) of waveform 600. The width or time of parameter $P_3^d$ is determined by counting the number of individual waveform pressure amplitude signals or samples generated by transducer 26A which lie above points 626 and 628 on waveform 600. If points 626 and 628 fall between individual waveform pressure amplitude signals or samples, interpolation is used to determine the time width of parameter $P_3^d$.

Parameter $P_4^d$ is identical to parameter $P_4^s$ used to calculate systolic blood pressure. Parameters $P_5^d$ and $P_6^d$ are calculated from absolute waveform pressures as illustrated in FIG. 4. Preferably, parameter $P_5^d$ is the diastolic pressure value of the uncorrected waveform having the largest maximum pressure value. Parameter $P_6^d$ is the diastolic pressure value of the uncorrected waveform (waveform 500) immediately following the waveform (waveform 500) having the largest maximum pressure amplitude or peak. Parameter $P_6^d$ is represented by point 730 on FIG. 4.

Parameter $P_7^d$ is derived from absolute waveform pressures illustrated in FIG. 4. To derive parameter $P_7^d$, the slopes along the portions of each individual waveform are determined. Parameter $P_7^d$ is the hold down pressure applied to the underlying artery that corresponds to the point on the particular waveform having the maximum slope corrected amplitude. The slope corrected amplitude of a waveform is obtained by multiplying its amplitude with the maximum slope over all waveforms and dividing the result with the slope corresponding to the individual waveform. As can be appreciated, various alternative parameters may also be used to calculate blood pressure values under the method of the present invention.

In preferred embodiments of the present invention, the waveform analysis described in U.S. Pat. No. 5,738,103 entitled "Segmented Estimation Method" and U.S. Pat. No. 5,720,292 entitled "Beat Onset Detector" are also used.

Although the present invention has been described with reference to preferred embodiments, workers skilled in the art will recognize that changes may be made in form and detail without departing from the spirit and scope of the invention. For example, although the determination of pressure values based upon waveform parameters has been described using linear equations and stored coefficients, other methods using non-linear equations, look-up tables, fuzzy logic and neural networks also can be used in accordance with the present invention.

In other embodiments, algorithms can be used that compensate for a non-linear hold down pressure sweep. This is accomplished by recording hold down pressure and pulse shape, so that the operation does not perform a linear sweep. A linear sweep can be constructed as long as there are several pulse shapes recorded over the range of the sweep, regardless of the order they are recorded.

Although the present invention has been described with reference to preferred embodiments, workers skilled in the art will recognize that changes may be made in form and detail without departing from the spirit and scope of the invention.

What is claimed is:

1. A method for determining blood pressure of an artery having a pulse, the method comprising:
   applying pressure to the artery with a flexible body comformable wall;
   sensing pressure data produced by the artery via a fluid filled chamber proximate to the wall;
   sensing noise data associated with the wall;
   correcting the pressure data based upon the noise data to produce corrected pressure data;

deriving a plurality of parameters from the corrected pressure data; and determining a blood pressure value based upon the parameters.

2. The method of claim 1 wherein sensing noise data comprises sensing pressure applied to the artery.

3. A method for determining blood pressure of an artery, the method comprising:

applying pressure to the artery with a flexible body conformable wall so that the artery exhibits a plurality of pressure waveforms;

producing sensed pressure waveform data representing each of the plurality of pressure waveforms via a fluid filled chamber proximate to the wall;

producing noise data sensed in the wall which is representative of noise contained in the pressure waveforms;

correcting the sensed pressure waveform data based on the noise data to produce corrected pressure waveform data;

deriving a plurality of parameters from the corrected pressure waveform data; and determining a blood pressure value based upon the parameters.

4. A non-invasive blood pressure measurement device, the measurement device comprising:

a flexible, body conformable wall for applying pressure to an artery so that the artery exhibits pressure data;

first sensing means for sensing the pressure data where the first sensing means includes a constant volume, fluid-filled chamber and a first pressure sensor;

second sensing means for sensing noise data associated with the body conformable wall;

signal producing means connected to the first and second sensing means for producing output signals corresponding to the sensed pressure data; and processing means for receiving the output signals from the signal producing means, for deriving a plurality of parameters using sensed pressure corrected to remove noise and for determining a blood pressure value using the derived parameters.

5. The measurement device of claim 4 wherein the first and second sensing means are mounted on a sensor interface assembly which is pivotally connected to a housing.

6. A non-invasive blood pressure measurement system comprising:

means for applying pressure to an artery with a flexible body comformable wall;

means for sensing pressure from the artery over time while the pressure is applied to the artery to generate pressure data;

means for sensing noise associated with the wall; and means for deriving a pressure value based upon a waveform analysis of the pressure data as corrected with the noise data.

7. A method of determining blood pressure, the method comprising:

applying pressure to an artery with a flexible body comformable wall;

sensing pressure over time via a fluid filled chamber proximate to the wall while pressure is applied to the artery to generate pressure waveform data for pressure waveforms representing a plurality of beats;

sensing noise in the wall over time;

correcting the waveform data to remove the sensed noise;

detecting onset of the beats from the waveform data;

extracting waveform parameters using a detected onset of one of the beats; and determining a blood pressure value based upon the waveform parameters.

8. A method for determining blood pressure of an artery having a pulse, the method comprising:

applying pressure to the artery with a flexible body comformable wall;

sensing pressure data produced by the artery via a fluid filled chamber proximate to the wall;

correcting the pressure data by removing noise components associated with motion artifacts sensed in the wall;

deriving a plurality of parameters from the corrected pressure data; and determining a blood pressure value based upon the plurality of parameters and a stored set of coefficients.

9. A device for external measurements of blood pressure in an underlying artery surrounded by tissue of a patient, the device comprising:

a flexible body comformable wall;

first sensing means includes a constant volume fluid-filled chamber which proximate to and isolated from the wall for sensing blood pressure pulses in the underlying artery;

second sensing means associated with the wall for sensing noise arising from motion artifacts that affect the wall and first sensing means;

means for applying a variable pressure to the artery through the wall; and means for calculating blood pressure from the sensed blood pressure pulses corrected to remove noise, based upon shape of the sensed pressure pulses within the underlying artery.

10. The device of claim 9, wherein the first sensing means includes:

a first transducer having a sensing surface;

a first flexible diaphragm for being positioned over the underlying artery; and first interface means between the first flexible diaphragm and the sensing surface of the first transducer for transmitting pressure pulses from the first flexible diaphragm to the first transducer.

11. The device of claim 10, wherein the second sensing means includes:

a second transducer having a sensing surface;

a second flexible diaphragm; and second interface means between the second flexible diaphragm and the sensing surface of the transducer for transmitting pressure from the second flexible diaphragm to the second transducer.

12. A device for sensing blood pressure within an underlying artery of a patient, the device comprising:

a first fluid filled sensing chamber having a diaphragm;

a first transducer fluidly coupled to the first fluid filled sensing chamber, wherein the first transducer senses fluid pressure within the first chamber;

a flexible body comformable wall proximate to the sensing chamber and isolated from the sensing chamber for applying force to the artery while preventing pressure in a direction generally parallel to the artery from being applied to the sensing chamber, the wall including a second fluid filled chamber; and a second transducer fluidly coupled to the second fluid filled chamber wherein the second transducer senses fluid pressure within the second chamber.

13. The device of claim 12, and further comprising:
means for deriving blood pressure values based upon signals from the first and second transducers.

14. A method of determining blood pressure, the method comprising:
applying a varying pressure to an artery;
sensing pressure data produced by the artery;
associating the pressure data with beats;
arranging the beats in an order that is a function of the pressure applied to the artery as it varies with each beat;
deriving a plurality of parameters from the pressure data; and
determining a blood pressure value based upon the plurality of parameters.

15. The method of claim 14, wherein arranging the beats places the beats in order of increasing hold down pressure.

16. A method of determining blood pressure, the method comprising:
applying varying pressure to an artery;
sensing pressure data produced by the artery during a plurality of beats;
arranging the pressure data associated with the beats as a function of the pressure applied to the artery as it varies with each beat;
deriving waveform parameters from the arrange pressure data; and
determining a blood pressure value based upon the waveform parameters.

17. The method of claim 16, and further comprising:
producing a signal representative of applied pressure.

18. The method of claim 17, wherein arranging the pressure data is based upon the signal representative of applied pressure.

19. The method of claim 16, wherein arranging the pressure data comprises:
associating pressure data with beats; and
ordering the beats based upon the applied pressure during each of the beats.

20. The method of claim 19, wherein the beats are arranged in order of increasing applied pressure.

21. A method for determining blood pressure of an artery, the method comprising:
applying a varying hold down pressure to the artery;
producing sensed pressure waveform data representing each of a plurality of pressure waveforms exhibited by the artery;
ordering the sensed pressure waveform data based upon a predetermined criteria that is a function of the hold down pressure as it varies with each of the pressure waveforms exhibited by the artery;
deriving a plurality of parameters from the sensed pressure waveform data; and
determining a blood pressure value based upon the parameters.

22. The method of claim 21, and further comprising:
sensing hold down pressure applied to the artery.

23. The method of claim 21, wherein ordering the sensed pressure waveform data arranges the sensed pressure waveform data in order of increasing hold down pressure.

24. A method of determining blood pressure, the method comprising:
applying varying pressure to an artery;
sensing pressure over time while the pressure is applied to the artery to generate pressure waveform data for pressure waveforms representing a plurality of beats;
ordering the beats based upon a predetermined criteria that is a function of the pressure applied to the artery as it varies with each beat;
extracting waveform parameters trom the pressure waveform data of the ordered beats; and
determining a blood pressure value based upon the waveform parameters.

25. The method of claim 24, wherein ordering the beats places the beats in order of increasing applied pressure.

26. The method of claim 24, wherein the predetermined criteria is pressure applied during each of the beats.

* * * * *

UNITED STATES PATENT AND TRADEMARK OFFICE
CERTIFICATE OF CORRECTION

PATENT NO. : 6,132,382
DATED : October 17, 2000
INVENTOR(S) : G. Kent Archibald

It is certified that error appears in the above-identified patent and that said Letters Patent is hereby corrected as shown below:

Column 14,
Line 63, after "via a", insert -- constant volume --
Line 64, after "wall", insert --, where the chamber transmits pressure from the artery to a first pressure sensor --
Line 65, after "wall", insert -- with a second pressure sensor --

Column 15,
Line 13, after "via a " insert -- constant volume --
Line 14, after " wall", insert --, where the chamber transmit pressure from the atery to a first pressure sensor --
Line 16, after "wall", insert -- via a second pressure sensor --
Line 34, before "signal", insert -- first --; and delete "and second"
Line 36 after "data", insert -- exhibited by the artery --
Line 36, before "and", insert -- second signal producing means connected to the second sensing means for producing output signals corresponding to the sensed noise data; --
Line 38, after "the", insert -- first and second --
Line 49, after "time", insert -- with a constant volume fluid filled chamber --
Line 50, after "artery", insert -- by the wall --
Line 60, after "via a", insert -- constant volume --
Line 61, after "wall", insert -- ,which transmits pressure to a first pressure sensor --
Line 62, after "artery", insert -- by the wall --
Line 64, after "time", insert -- with a second pressure sensor --

Column 16,
Line 10, after "via a", insert -- constant volume --
Line 11 after "wall", insert -- where the chamber transmit pressure from the artery to a first pressure sensor --
Line 14, after " wall", insert -- with a second pressure sensor --
Line 23, delete "includes a constant volumn fluid-filled chamber which"
Line 26, after "artery", insert -- where the first sensing means includes a constant volumne fluid filled chamber which transmits the pressure pulses to a first signal producing means --
Line 29, after "artery", insert -- where the second sensing means transmits sensed noise to a second signal producing means --
Line 31, delete "through", insert -- with --

UNITED STATES PATENT AND TRADEMARK OFFICE
CERTIFICATE OF CORRECTION

PATENT NO. : 6,132,382
DATED : October 17, 2000
INVENTOR(S) : G. Kent Archibald

It is certified that error appears in the above-identified patent and that said Letters Patent is hereby corrected as shown below:

Column 17,
Line 11, after "beats", insert -- which are in a first order that is a function of time --
Line 12, delete "an", insert -- a second --
Line 24, after "beats", insert -- which are in the first order that is a function of time --
Line 25, delete "as", insert -- in a second order that is --
Line 28, delete "arrange", insert -- arranged --

Column 18,
Line 6, after "data", insert a first order that is a function of time --
Line 9, after "data", insert -- in a second order --
Line 27, after " beats", insert -- , which are in a first order that is a function of time --
Line 28, after "beats", insert -- in a second order --
Line 31, delete " trom, insert -- from --

Signed and Sealed this

Twenty-sixth Day of March, 2002

Attest:

JAMES E. ROGAN
*Attesting Officer*     *Director of the United States Patent and Trademark Office*